(12) United States Patent
Watabe et al.

(10) Patent No.: US 9,476,894 B2
(45) Date of Patent: Oct. 25, 2016

(54) CENTRIFUGE MODULE, PREPROCESSING SYSTEM HAVING CENTRIFUGE MODULE, AND CONTROL METHOD FOR THE SYSTEM

(71) Applicant: HITACHI HIGH-TECHNOLOGIES CORPORATION, Tokyo (JP)

(72) Inventors: Osamu Watabe, Tokyo (JP); Shigeru Yano, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 179 days.

(21) Appl. No.: 14/398,477

(22) PCT Filed: May 24, 2013

(86) PCT No.: PCT/JP2013/064429
§ 371 (c)(1),
(2) Date: Nov. 3, 2014

(87) PCT Pub. No.: WO2013/180017
PCT Pub. Date: Dec. 5, 2013

(65) Prior Publication Data
US 2015/0111299 A1    Apr. 23, 2015

(30) Foreign Application Priority Data

May 28, 2012   (JP) .................................. 2012-120374

(51) Int. Cl.
G01N 35/00    (2006.01)
G01N 1/18     (2006.01)
B04B 11/04    (2006.01)

(52) U.S. Cl.
CPC ..... *G01N 35/0095* (2013.01); *B04B 2011/046* (2013.01); *G01N 2035/00495* (2013.01); *G01N 2035/00752* (2013.01); *G01N 2035/00782* (2013.01); *Y10T 436/111666* (2015.01)

(58) Field of Classification Search
CPC ................................ G01N 35/00; G01N 1/18
USPC ........... 422/67, 72; 436/45, 177; 494/20, 37; 702/31
See application file for complete search history.

(56) References Cited

U.S. PATENT DOCUMENTS

| 6,060,022 A | 5/2000 | Pang et al. |
| 6,337,050 B1 * | 1/2002 | Takahashi ............ G01N 35/026 422/63 |

(Continued)

FOREIGN PATENT DOCUMENTS

| JP | 11-304806 A | 11/1999 |
| JP | 2001-505648 A | 4/2001 |

(Continued)

*Primary Examiner* — Arlen Soderquist
(74) *Attorney, Agent, or Firm* — Mattingly & Malur, PC (57) ABSTRACT

When a STAT sample which needs to be centrifuged is inputted in the system, a measure to quickly realize centrifugation of the STAT sample is necessary. In view of the foregoing problem, the invention provides a specimen processing and conveying system in which a centrifuge module incorporated, the centrifuge module being capable of discriminating the operation status of the system at the time point when a STAT sample is inputted and the attribute of the inputted sample and starting centrifugation operation on the basis of the input interval of samples or the arrival interval at the device carrying out centrifugation, and thus capable of starting centrifugation operation quickly when a single or a group of plural samples of urgency is inputted.

11 Claims, 5 Drawing Sheets

(56) References Cited

U.S. PATENT DOCUMENTS

| | | |
|---|---|---|
| 2006/0116269 A1 | 6/2006 | Lagarde |
| 2007/0020764 A1* | 1/2007 | Miller ................ G01N 35/0092 436/45 |
| 2007/0059209 A1* | 3/2007 | Pang ................ G01N 35/0095 422/72 |
| 2009/0318276 A1* | 12/2009 | Miller .................... B04B 13/00 494/20 |
| 2010/0250174 A1* | 9/2010 | Tokunaga ........... G01N 35/0092 702/83 |
| 2011/0003674 A1* | 1/2011 | Fox ...................... B04B 5/0414 494/7 |
| 2011/0045958 A1* | 2/2011 | Pedrazzini ............ B04B 5/0421 494/8 |
| 2012/0094368 A1* | 4/2012 | Dee ................... G01N 35/0095 435/287.2 |
| 2012/0129673 A1 | 5/2012 | Fukugaki et al. |
| 2012/0177548 A1 | 7/2012 | Suzuki et al. |
| 2013/0117042 A1* | 5/2013 | Tajima ............... G01N 35/0092 705/2 |
| 2013/0123089 A1* | 5/2013 | Johns ................... B01D 21/262 494/37 |
| 2013/0281279 A1* | 10/2013 | Yagi ....................... B04B 9/146 494/1 |
| 2015/0360239 A1* | 12/2015 | Yano ....................... B04B 13/00 494/10 |

FOREIGN PATENT DOCUMENTS

| | | |
|---|---|---|
| JP | 2005-533641 A | 11/2005 |
| JP | 2011-025181 A | 2/2011 |
| WO | 2011/039932 A1 | 4/2011 |

* cited by examiner

CENTRIFUGE MODULE, PREPROCESSING SYSTEM HAVING CENTRIFUGE MODULE, AND CONTROL METHOD FOR THE SYSTEM

TECHNICAL FIELD

The present invention relates to a specimen processing system having an input buffer module for supplying a sample and a centrifuge module for centrifuging an inputted sample.

BACKGROUND ART

In hospitals and test institutions, blood, urine and other samples are analyzed for clinical examinations. Samples taken from patients are not necessarily placed in an analyzer as they are and may be centrifuged as preprocessing for analysis and subdivided for analysis. A system in which such a preprocessing flow or a flow from the preprocessing to the analysis is automated is called a specimen processing and conveying system.

PTL 1 discloses a typical specimen processing and conveying system having an automatic centrifuge unit. In the specimen processing and conveying system, a centrifuge module is disclosed which revolves at high speeds in the state where plural adapters holding plural sample tubes are installed, thus centrifuging the samples. Several ten sample tubes can be processed in one session of centrifugal processing. Also, since centrifugation may take approximately ten minutes, centrifugal processing is not started until a certain number of sample tubes are accumulated after sample tubes are inputted, and centrifugal processing is started after sufficient sample tubes are accumulated, thus enhancing processing efficiency.

CITATION LIST

Patent Literature

PTL 1: JP-A-2011-025181

SUMMARY OF INVENTION

Technical Problem

As described above, the automatic centrifuge unit performs batch processing of plural samples that arrive there. Since centrifugal operation is not started while it is possible to retain the arriving sample tubes, it may take time until centrifugal processing is started after the sample tubes are inputted. Therefore, centrifugal operation is regarded as one of the most time-consuming types of processing in the system.

Meanwhile, in the specimen processing and conveying system, a sample that need to be processed urgently (STAT sample) is inputted as well as routine samples. The input timing of a STAT sample is irregular. It is common that a STAT sample is inputted, interrupting the course of input of routine samples online. However, since the result of analysis of a STAT sample needs to be reported urgently, preprocessing thereof needs to be carried out quickly. Meanwhile, in the conventional specimen processing and conveying system, as described above, since centrifugal processing is not started until a predetermined amount of samples are accumulated, a STAT sample that needs to be centrifuged cannot be processed quickly in some cases.

In view of the foregoing problem, an object of the invention is to realize a specimen processing and conveying system in which centrifugal processing on a STAT sample is carried out quickly without lowering the processing speed for routine samples.

Solution to Problem

A configuration of the invention to solve the foregoing problem is as follows.

That is, the configuration includes: a centrifuge module capable of performing simultaneous centrifugal processing on a maximum number of samples or fewer, registered as a centrifuge set; an identification unit which identifies arrival of a sample; a registration unit which adds and registers the sample identified by the identification unit, to the centrifuge set; and a control unit which performs control to finalize the centrifuge set if a predetermined condition is satisfied, and to perform simultaneous centrifugal processing on the samples registered as the finalized centrifuge set.

Advantageous Effect of Invention

A STAT sample is inputted irregularly into the specimen processing and conveying system. Therefore, the arrival at the automatic centrifuge unit and the timing when the STAT sample is centrifuged, vary depending on the operating status of the system at the time when the STAT sample is inputted.

The invention enables centrifugal operation to be started even when all of the maximum number of samples that can be centrifuged simultaneously are not gathered, on the basis of attributes of the inputted sample (STAT sample/routine sample, requested test orders and the like), and the input interval and arrival interval of the sample. This enables centrifugal operation to be started flexibly and quickly even when a STAT sample is inputted.

Also, the start of centrifugal operation can be realized without lowering the efficiency of centrifugal operation even when plural STAT samples are inputted.

DESCRIPTION OF EMBODIMENTS

Embodiments based on the invention will be described, using the drawings.

Figure 5:
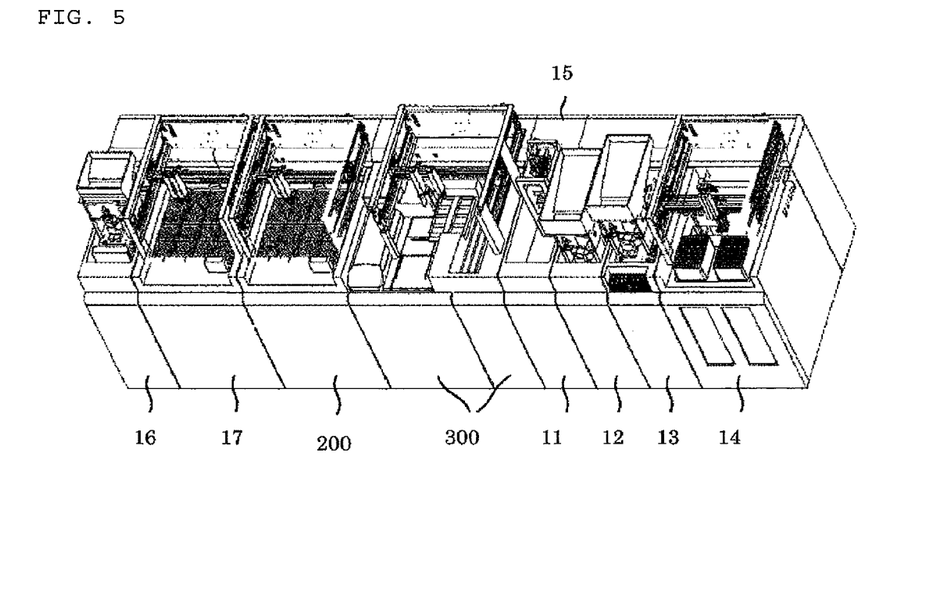
FIG. 5 is a general view of a specimen processing and conveying system according to an embodiment of the invention.

FIG. 5 is a general view of a specimen processing and conveying system according to the invention.

In FIG. 5, 200 is an input buffer module. An original sample is usually inputted into the specimen processing system from the input buffer module 200. 300 is a centrifugal processing unit, which automatically installs a sample in a rotor inside a centrifuge and performs centrifugation, and then automatically carries the sample out. 11 is an automatic stopper opening unit, which automatically extracts a stopper. 12 is an automatic barcode pasting unit, which automatically pastes a barcode label onto a container such as a test tube. 13 is a container and carrier supply unit, which automatically installs the container in a carrier and carries the container out. 14 is an aliquoter unit, which ejects an aliquot sample into another container from the centrifuged original sample.

The original sample is aliquoted by the aliquoter unit 14, generating one or more aliquot samples. The aliquot sample is a sample generated to be analyzed by an automatic analyzer and is carried out directly to a conveyer line connected to the automatic analyzer without going through any other unit from the aliquoter unit 14 and is delivered to the automatic analyzer.

The original sample is carried through a return conveyer line 15 provided inside the automated specimen processing system. A stopper is mounted on the container containing the sample by a restopper module 16, and the container is housed in a housing unit 17. As a line is provided which is orthogonal to the conveyer line carrying the aliquot sample or original sample out on which processing is finished and the return line 15 is provided inside the automated specimen processing system, carrying of the sample carried to the automatic analyzer within a minimum time without passing through another unit is realized.

The system configuration view of FIG. 5 is an example. In practice, the scale and the application method vary from user to user. Therefore, there are cases where plural specimen processing systems are installed or cases where plural processing units are formed within one specimen processing system.

Also, in consideration of the installation area, convenience in terms of application, and the estimated cost or the like, it is possible to add a necessary processing unit or remove an unnecessary processing unit from the specimen processing system. By increasing analyzer connection lines, it is also possible to connect to plural automatic analyzers. The specimen processing system can be configured freely and flexibly for user convenience.

Figure 1:
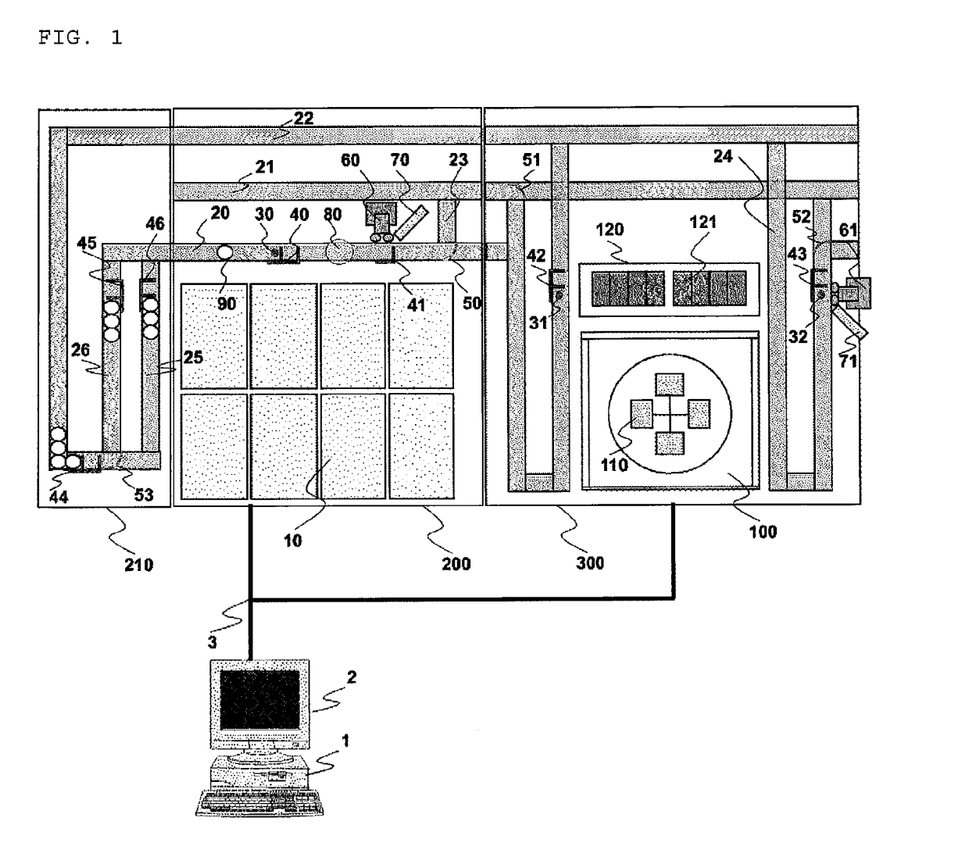
FIG. 1 shows a part of a specimen processing and conveying system according to an embodiment of the invention.

FIG. 1 shows a block diagram of the input buffer module 200 and the centrifuge module 300.

The input buffer module 200 shifts a sample inputted in the state of being installed on a sample input tray 10 onto an empty carrier 90 waiting at a stopper mechanism 40, by a sample chuck mechanism (not shown). The waiting carrier has the carrier ID thereof identified in advance by a carrier ID reading mechanism 30.

Each carrier 90 onto which the sample is shifted has the weight thereof measured by a weight measurement mechanism 80, and subsequently the sample ID is read by a sample barcode reader 70 at a stopper mechanism 41. Based on the sample ID thus read, sample attributes (whether centrifugal processing is needed or not, routine sample/STAT sample, requested test orders) are acquired and added to the centrifuge set. Also, the sample ID thus read and the carrier ID are associated with each other and stored in an operation unit computer 1.

In the invention, a centrifuge set means an aggregate of samples to be centrifuged in a single session of processing. In the case of the centrifuge module 300 of FIG. 1, an adapter bucket mechanism 110 capable of holding four adapters 121 in a single session of processing is provided. If the number of sample tubes that can be installed in one adapter is nine, it is possible to centrifuge 4×9=36 sample tubes in a single session of processing, and 36 sample tubes at maximum form one centrifuge set.

The centrifuge module 300 controls the timing of starting centrifugal operation on the sample on the basis of centrifuge set information created by the input buffer module. Specifically, the ID information of the carrier 90 arriving at a stopper mechanism 42 is read by a carrier ID reading mechanism 31, and the sample ID information associated with the carrier ID in question is extracted from the operation unit computer 1. Based on the sample ID information thus extracted, it is determined whether the centrifuge set where centrifugal processing is carried out on the sample in question is the present centrifuge set or the next centrifuge set.

If it is determined as the present centrifuge set, the sample tube is shifted to a sample tube housing position in an adapter 121 on an adapter holding mechanism 120 by a sample chuck mechanism (not shown). Meanwhile, if it is determined as the next centrifuge set, the sample chuck mechanism does not chuck the sample tube in question. The adapter is shifted into the adapter bucket mechanism 110 by an adapter gripper mechanism (not shown), and centrifugal processing is then started.

The information sharing between the input buffer module 200 and the centrifuge module 300 is carried out via an interface 3 with the operation unit computer 1 having an operation function. However, a method in which parameter information such that the start of centrifugation is triggered by an arrival interval of samples is received from the operation unit computer 1, and then centrifugal operation is started while determining the arrival time of the sample arriving at the centrifuge module, may be employed.

Example 1

Figure 6:
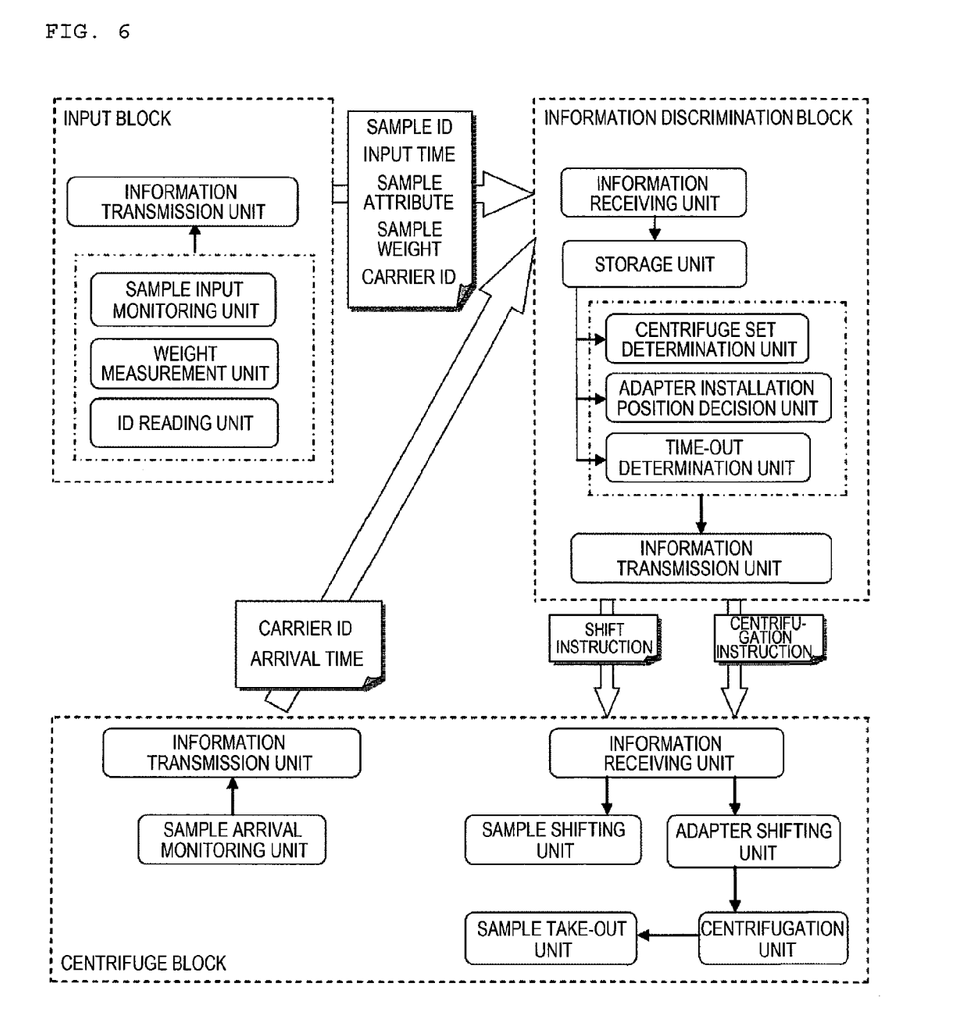
FIG. 6 is a functional block diagram according to an embodiment of the invention.

Functional blocks to carry out Example 1 of the invention are shown in FIG. 6. In the invention, an input block for monitoring that a sample is inputted in the system, a centrifuge block for actually executing centrifugal processing, and an information discrimination block for managing information are included.

The input block has a sample input monitoring unit which monitors whether a new sample is inputted to a sample installation tray or a sample urgent input port, or not. Specifically, the unit is an RFID antenna or optical sensor for reading an RFID tag attached to the sample installation tray. As a sample is inputted, the time when the sample is inputted is acquired as input time information.

An ID reading unit reads the ID of an inputted sample and the ID of a carrier on which the sample in question is loaded. For example, a barcode reader for reading a barcode label attached to the lateral side of a sample tube, or an RFID reader for reading information stored in an RFID tag attached to a carrier is equivalent to this. Also, sample attribute information is read in addition to the sample ID, from the barcode label attached to the sample tube.

A weight measurement unit is a weight sensor such as a load cell and acquires the weight of an individual sample that is inputted.

The sample attribute information, the sample weight information, and the carrier ID information are associated with the acquired sample ID information and transmitted to the information discrimination block via an information transmission unit.

The centrifuge block has a sample arrival monitoring unit which monitors whether a sample arrives at the centrifuge module or not. Specifically, an RFID antenna or optical sensor for detecting arrival of a carrier is provided at the entrance of the centrifuge module. As the arrival of a carrier is detected by the sample arrival monitoring unit, the carrier ID information of the arriving carrier and the time when the arrival of the carrier is detected (arrival time information) are acquired. The carrier ID information and the arrival time information thus acquired are transmitted to the information discrimination block via an information transmission unit.

In the information discrimination block, the information transmitted from the input block and the centrifuge block is received by an information receiving unit and stored in a storage unit. Also, in the information discrimination block, a centrifuge set setting unit which creates a centrifuge set, a time-out determination unit which sets and monitors a time-out, and an adapter installation position decision unit which decides on the position to load a sample tube, are provided.

The centrifuge set setting unit determines whether to include the sample in question in a centrifuge set or not, on the basis of the sample ID information and the associated sample weight information, transmitted from the input block. If the sample is determined as to be included in the centrifuge set, an adapter to load the sample in question is finalized by the adapter installation position decision unit.

The time-out determination unit determines whether a time-out occurs or not, on the basis of the sample input time received from the input block and the sample arrival time received from the centrifuge block. If it is determined that a time-out occurs, time-out information is transmitted to the centrifuge set setting unit to finalize the centrifuge set.

As the centrifuge set and the adapter installation position are finalized, the information discrimination block transmits shift instruction information of the sample to the centrifuge block via an information transmission unit. Also, if the time-out determination unit determines a time-out occurs, centrifugation instruction information is transmitted.

In the centrifuge block, an information receiving unit receives these pieces of information. A sample shifting unit (for example, a sample chuck mechanism or the like) has a function of chucking a sample tube and shifting the sample tube from a carrier to an adapter, and installs a sample arriving at the centrifuge module onto an appropriate adapter on the basis of the shift information of the sample transmitted from the information discrimination block. An adapter shifting unit (for example, an adapter gripper mechanism) has a function of holding an adapter and shifting the adapter between an adapter standby position and the centrifuge, and carries an adapter with a sample installed therein into the centrifuge on the basis of the centrifugation instruction information from the information discrimination block. Moreover, a centrifugation unit starts centrifugal processing as all the adapters are carried in.

As centrifugal processing ends, information to that effect is transmitted to a sample take-out unit from the centrifugation unit, and the sample tube on which centrifugal processing is finished is placed on the carrier and taken out from the centrifuge module.

It should be noted that the information discrimination block illustrated in the above functional block diagram need not be entirely provided within the operation unit computer 1 and may be partly incorporated in the control unit of the input buffer module or the centrifuge module.

Figure 4:
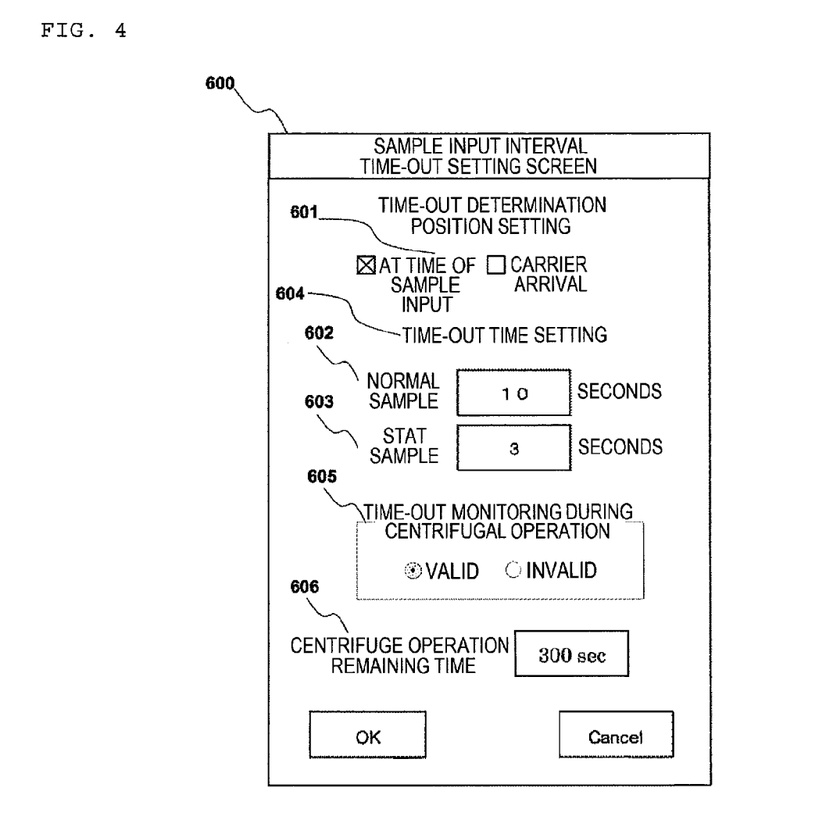
FIG. 4 shows a screen to register the setting of a centrifugation start determination condition according to the invention.

Next, a time-out setting method will be described, using FIG. 4.

Prior to the processing, in this specimen processing and conveying system, an operator designates a behavior in the case where a STAT sample is inputted, via the operation unit computer 1. A sample input interval time-out setting screen 600 is displayed on an operation unit computer display 2 of the operation unit computer 1. The operator can set a time-out determination position designation 601, a routine sample time-out time designation 602, and a STAT sample time-out time designation 603, via an input unit such as a keyboard, mouse, or touch panel.

The time-out determination position designation 601 is to set whether the interval at which samples are inputted to the input buffer module 200 is taken as a start point of time-out, the time interval between the time point when a sample arrives at the centrifuge module 300 and when the next sample arrives is taken as a start point of time-out, or both of these are taken as start points of time-out.

Since the time when sample is inputted to the input buffer module 200, the time when a carrier arrives at the centrifuge module 300, or both of these can be designated as the timing of determining a time-out, flexible measures can be taken even if the input interval is increased in the case where the amount of samples on the tray 10 in the input buffer module 200 is small, or if a delay in the carrying to the centrifuge module 300 is generated by stagnation or the like of sample carriers 90 on the line laid in the device due to a certain factor.

In a time-out time setting 604, a time-out time can be set for each of the routine sample 602 and the STAT sample 603. In the case of FIG. 4, with respect to routine samples, if the next sample is not detected at the determination position for ten seconds or longer, it is determined that there is a time-out. Meanwhile, with respect to STAT samples, if the next sample is not detected at the determination position for three seconds or longer, it is determined that there is a time-out. If it is determined that there is time-out, the samples inputted up to that time point are finalized as forming a centrifuge set, and the samples that are subsequently inputted are included in the next centrifuge set. As described above, generally, it is desirable that the time-out time for STAT samples is made shorter than for routine samples because it enables early start of centrifugal processing of the STAT sample. While the operator can set time-out times for routine samples and STAT samples in this example, the time-out times may be set as fixed parameters on the side of the device.

If a maximum number of samples in a centrifuge set continuously arrive at the determination position without having a single preset time-out, the centrifuge set is finalized at the time point when the maximum number in the centrifuge set is reached, and the sample tube that is subsequently inputted is determined as forming the next centrifuge set. In the centrifuge set in question, centrifugal processing is to be performed on a maximum number of samples that can be installed in the adapters 121.

As the routine sample time-out time designation 602 and the STAT sample time-out time designation 603 are set separately, when a STAT sample is inputted, the processing on the inputted STAT sample can be carried out preferentially over the processing capability of the entire specimen processing and conveying system. Moreover, if the STAT sample time-out time designation 603 is designated as "0 seconds", when the presence of a STAT sample in the system in question is detected at the determination position, the centrifuge set is immediately finalized and control of centrifugal operation on a single sample basis can be realized.

Moreover, as a setting of time-out monitoring during centrifugal operation 605 is provided, whether to monitor a time-out during centrifugal operation or not can be switched. When the time-out function of the automatic centrifuge unit is used, there are cases where centrifugal operation may be started even in the state where a maximum number of samples that can form one centrifuge set are not installed on the adapters. Particularly, if plural samples are inputted intermittently or in the state where the input intervals are uneven, the above tendency becomes conspicuous and can end up with a centrifuge set formed by a small number of samples, thus leading to a fall in the processing efficiency of the system as a whole. In order to avoid this fall in efficiency, the setting of time-out monitoring during centrifugal operation 605 can be set to "invalid" while centrifugal processing is executed on the previous centrifuge set on the side of the centrifuge module.

Also, in the sample input interval time-out setting screen 600, a centrifuge operation time display section 606 for confirming the operation status of the centrifugal rotor in the centrifuge module is provided. In this section, the remaining time to be taken until the operation of the centrifuge stops is displayed. When centrifugal processing is not carried out and the centrifuge is stopped, "0" is displayed.

After setting the above parameters, the operator installs the sample input tray 10 on which samples are laid, in the input buffer module 200, and starts specimen processing operation. In the input buffer module 200 of this system, eight sample input trays 10 at maximum can be installed simultaneously and the sample input trays 10 can be replaced even during the execution of the specimen processing operation. Therefore, by replacing the sample input tray 10 that becomes empty after the samples installed on the sample input tray 10 are inputted in the system, it is possible to input samples continuously. Also, in the input buffer module 200, it is possible for the operator to input a sample that the operator wants to be processed urgently, apart from the samples installed on the sample input tray 10 and processed as routine work.

Figure 2:
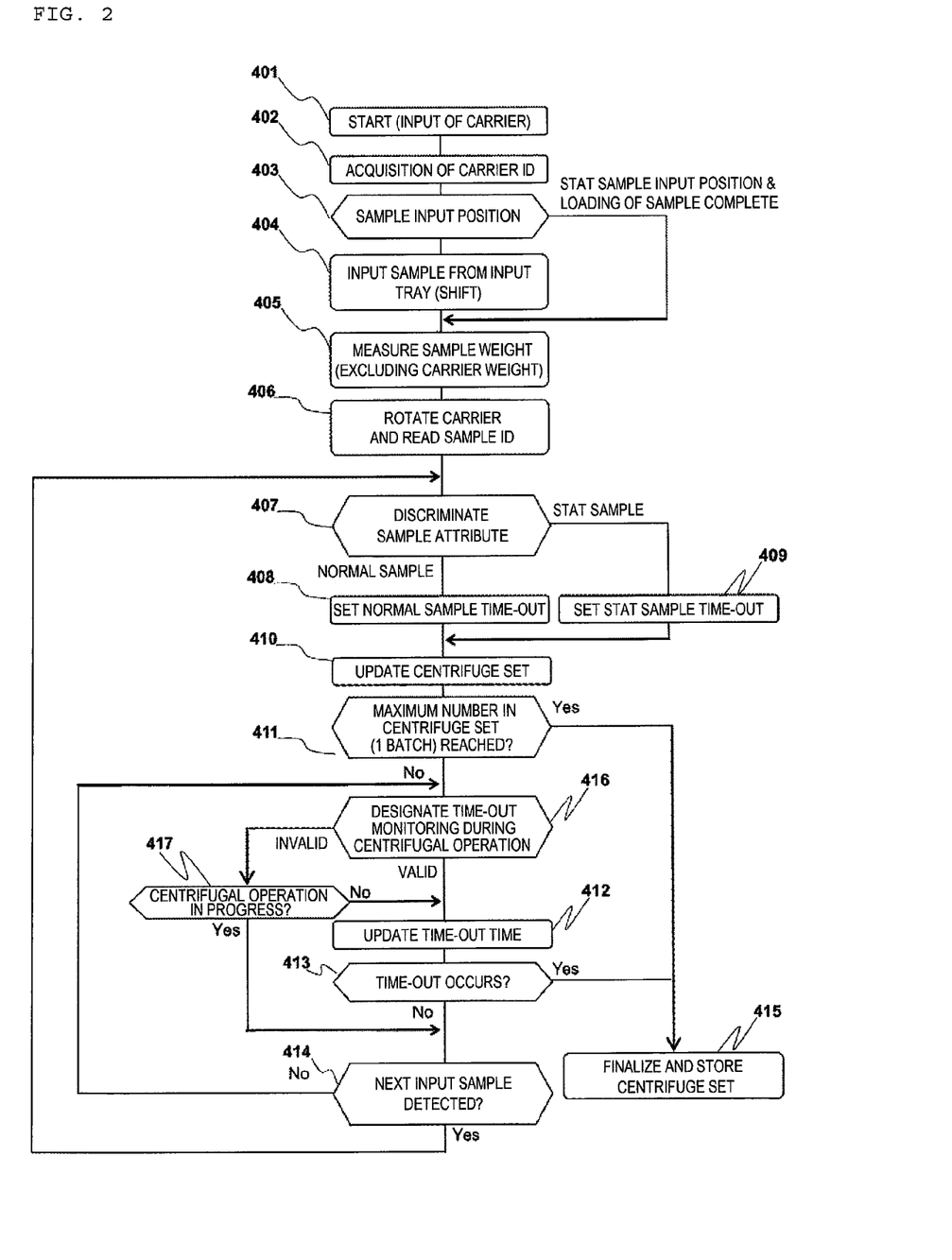
FIG. 2 is a flowchart of centrifuge set information update operation with an inputted sample.

Next, the carrying operation and processing when the time-out determination position is defined as "at the time of sample input" will be described, using FIG. 2.

The carrier 90 carrying a sample inputted in the specimen processing system has an information recording medium having unique ID information. As the information storage medium, ID management by RFID may be employed, or a barcode label, IC tag or the like may be used.

When a new sample is inputted in the specimen processing and conveying system in question, the carrier 90 is supplied to the sample conveyer line 20 in the input buffer module 200. Also, when the carrier becomes unnecessary for the use in the system (when the sample loaded thereon is extracted), the carrier is collected to an empty carrier circulation conveyer line 22 from the sample conveyer line 20. Also, the present status of use of the carrier 90 used in the system can be grasped by reading the ID at the time of supply or collection, thus enabling repetitive use in the application in the system in question.

The carrier 90 for loading a sample inputted from the input buffer module 200 goes around through the empty carrier circulation conveyer line 22 and is stored on a carrier stocker 210. The carrier stocker 210 has a routine sample empty carrier supply conveyer line 25 and a STAT sample empty carrier supply conveyer line 26.

When a routine sample loaded on the installation tray is inputted, the carrier 90 is supplied from the routine sample empty carrier supply conveyer line 25 onto the sample conveyer line 20 and carried to the input buffer module 200. Meanwhile, when a STAT sample is inputted, the carrier 90 is supplied from the STAT sample empty carrier supply conveyer line 26 to the sample conveyer line (sample carrier input step 401). For the input of a STAT sample, an input port dedicated for STAT samples may be provided. Alternatively, after a STAT sample is inputted at the same position as a routine sample, the input of the STAT sample may be recognized by reading the barcode label or the like or by an instruction from the operator.

After the STAT sample is loaded on the supplied carrier 90, the sample is carried into and through the system according to an intake instruction from the operator. When input operation of a STAT sample is carried out, control is performed so that the supply of the carrier 90 from the routine sample empty carrier supply conveyer line 25 is temporarily interrupted and then resumed after the input operation of the STAT sample is completed.

The carrier 90 carried on the sample conveyer line 20 has the ID information thereof read by the carrier ID reading mechanism 30 at the stopper mechanism 40 (sample carrier ID acquisition step 402).

After the reading of the carrier ID information is completed, the presence/absence of a sample on the inputted carrier 90, and if a sample is loaded, the position where the sample in question is inputted, are confirmed (sample input position determination step 403).

If there is no sample on the carrier 90, a sample on the sample input tray 10 is shifted onto the carrier 90 by the sample chuck mechanism (not shown) (sample input step 404), and the carrier 90 is carried into the system.

Meanwhile, if the sample input position is on the STAT sample empty carrier supply conveyer line 26 and there is a sample on the carrier 90 (that is, if the carrier is recognized as a carrier having a STAT sample loaded thereon), the carrier is carried into the system, without carrying out sample shifting operation on the sample input tray 10 by the sample chuck mechanism.

The carrier 90 holding a STAT sample or routine sample has the weight thereof measured by the weight measurement mechanism 80 in order to take a balance among adapters arranged in the rotor at the time of centrifugal processing (sample weight measurement step 405). In this weight measurement, the weight of the sample carrier 90 with a sample loaded thereon is subtracted from the actually measured weight, thus finding a more accurate weight. It is desirable that the weight of each carrier is grasped with the unique ID of the carrier.

The carrier in which weight measurement is completed is carried to the arriving sample stopper mechanism 41. While the container with a sample housed therein is rotated by a sample restraining and rotating mechanism 60, the barcode pasted on the sample tube is read by the sample barcode reader 70. The sample ID stored in the barcode is recognized. The sample ID, the sample attributes and the carrier ID are reported as a single piece of information to the operation unit computer 1 and stored in the operation unit computer 1 (sample ID acquisition step 406).

If the time-out determination position designation 601 designates a time-out based on the interval at which samples are inputted by the input buffer module 200, as a start point (if "at the time of sample input" is selected), the operation unit computer 1 determines the attributes of the inputted sample on the basis of the result of the barcode reading by the sample barcode reader 70 (sample attribute determination step 407), initializes the time-out time information about the interval until the next sample is inputted (time-out setting steps 408, 409), and adds the acquired sample information to the configuration information of the centrifuge set (centrifuge set information update step 410). The time-out time to be set varies depending on sample attribute. Specifically, if the sample attribute is a STAT sample, it is desirable that the time-out time is set to be shorter than in the case of a routine sample.

If "at the time of sample input" is not set by the time-out determination position designation 601, steps 407 to 409 are not carried out.

With the addition of the sample information in question, it is determined whether a maximum number of samples that can be processed in one session of centrifugal processing is reached or not (step 411). If the maximum number is reached, the centrifuge set information is stored as finalized control information, and management as new centrifuge set information is started with the next arriving sample and onward (centrifuge set information finalization step 415).

If the maximum number of samples that can be processed in one session of centrifugal processing is not reached after the sample information is added, the setting of time-out monitoring during centrifugal operation 605 is confirmed in step 416. If the setting of time-out monitoring during centrifugal operation 605 is set to "valid", the time-out time is updated (time-out update step 412) along with the centrifuge set information update step 410, and occurrence of a time-out is monitored (time-out occurrence monitoring step 413). If a time-out occurs the centrifuge set information finalization step 415 is executed. On the other hand, if the next sample is not inputted before the occurrence of a time-out, the processing return to the step 416 and repeat the monitoring the time-out. If it is detected that the next sample is inputted before the occurrence of a time-out (step 416), the accumulated time-out time is cleared, the processing shifts to the sample attribute determination step 407, and the similar processing is repeated subsequently.

Meanwhile, if the setting of time-out monitoring during centrifugal operation 605 is set to "invalid", at the step 416, whether the centrifugal operation of the centrifuge module is in progress or not is determined (step 417). The centrifugal operation in progress refers to the state where the centrifuge of the centrifuge module is revolving. If the centrifugal operation is not in progress, similar processing to the case where the setting of time-out monitoring during centrifugal operation 605 is set to "valid" is carried out. If the centrifugal operation is in progress, arrival of the next sample is waited for, without carrying out the time-out update step 412 and the time-out occurrence monitoring step 413. Also, even in the case where the setting of time-out monitoring during centrifugal operation 605 is set to "invalid" in this manner, as the centrifugal operation by the centrifuge ends, the processing shifts from the step 417 to the time-out update step 412 and the time-out occurrence monitoring step 413. Therefore, if the next sample does not arrive, the centrifuge set is finalized on the occurrence of a time-out.

Meanwhile, if a STAT sample is detected after the time-out rule for routine sample is applied, the rule is updated to the time-out rule for STAT sample. Even if arrival or input of a routine sample is detected subsequently, the rule for STAT sample is applied as the time-out rule. That is, if there is at least one STAT sample in the sample group forming the centrifuge set, the rule for STAT sample is applied as the time-out rule.

If there is no designation of setting a time-out based on the interval at which samples are inputted by the input buffer module 200, as a start point, the centrifuge set information update step 410, the centrifuge set information finalization step 415, and the next input sample detection determination step 414 are carried out without considering the finalization of the centrifuge set based on the occurrence of a time-out.

Since the sample weight measurement step 405 is provided, it is possible to draw up a schedule such that a weight balance is taken on a single inputted sample basis. That is, when the sample weight measurement step 405 is carried out on a newly inputted sample and the individual weight is acquired, if it is determined that the weight balance between the respective adapters cannot be maintained if the sample in question is carried into an adapter, the sample in question is not fed into the centrifuge module 300. With such control, whatever timing the centrifuge set is finalized at, the weight balance between the respective adapters is not disrupted in centrifugal processing.

The carrier 90 determined as not needing centrifugal operation on the inputted sample is delivered to an overtaking line 21 via an overtaking conveyer merging line 23 and carried to another processing unit. Also, in a system having plural centrifuge modules, the carrier is similarly delivered to the overtaking conveyer line 21 via the overtaking conveyer merging line 23 and carried to a centrifugal processing unit that is not adjacent.

Figure 3:
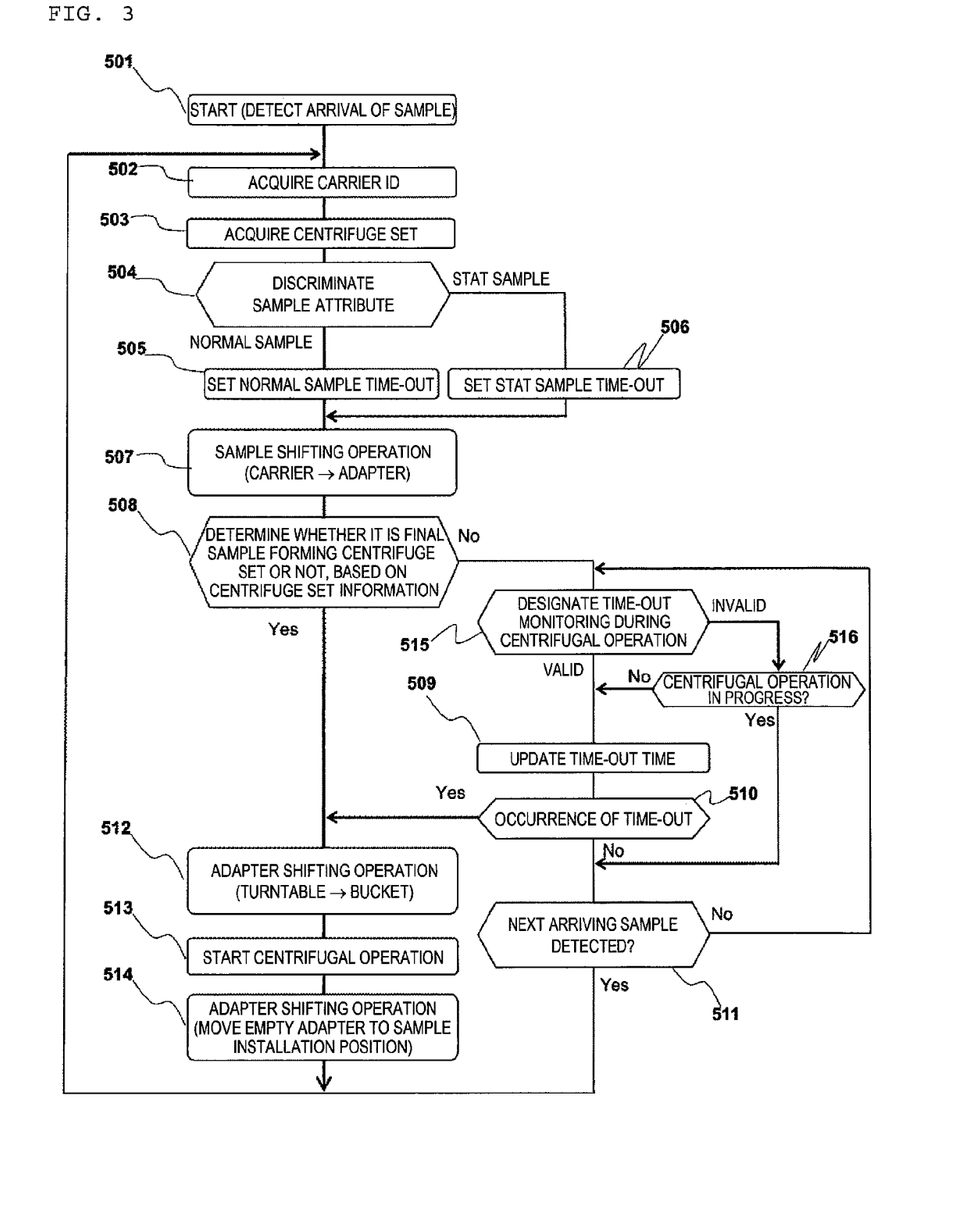
FIG. 3 is a flowchart of centrifugal operation determination operation with a sample arriving at a device having a centrifuge unit.

Next, the carrying operation and processing when the time-out determination position is designated as "carrier arrival" will be described, using FIG. 3.

The carrier 90 holding a sample that needs centrifugal operation is carried to an appropriate centrifuge module 300. After the carrier 90 is carried to the sample stopper mechanism 42 in the centrifuge module 300, arrival confirmation is carried out by a carrier detection sensor (not shown) (sample arrival detection step 501). As the arrival of the sample is confirmed, the carrier ID is read by the sample conveying carrier ID reading mechanism 31 (sample carrier ID acquisition step 502).

In the centrifuge module 300, the arrival of the sample is reported to the operation unit computer 1, using the read carrier ID information as key information, and centrifuge set information corresponding to the sample in question is acquired from the operation unit computer 1 as response information thereto (centrifuge set information acquisition step 503). If the time-out determination position designation 601 designates for setting a time-out based on the time interval from the time point when a sample arrives at the centrifuge module 300 to the arrival of the next sample, as a start point ("carrier arrival" is designated), the attribute of the sample is determined at the time point when the carrier ID is read by the sample conveying carrier ID reading mechanism 31 (sample attribute determination step 504), and the time-out time information is initialized (time-out setting steps 505, 506). If "carrier arrival" is not selected in the time-out determination position designation, the steps 504 to 506 are not carried out.

Again, the time-out time to be set varies depending on sample attribute. Specifically, if the sample attribute is a STAT sample, it is desirable that the time-out time is set to be shorter than in the case of a routine sample.

In the centrifuge module 300, on the basis of the acquired centrifuge set information, the arriving sample is extracted from the carrier 90 by the sample chuck mechanism (not shown) and shifted onto the adapter 121 on the adapter holding mechanism 120 (sample shifting step 507), and the operation after the sample shifting is determined (post-shifting processing determination step 508). Specifically, whether the sample shifted to the adapter in the sample shifting step 507 is the final sample that forms this centrifuge set or not is determined. If the sample is the final sample (in the case of Yes), all the samples forming the centrifuge set are already shifted to the adapters. Therefore, shifting operation of the sample installation adapters 121 is carried out by the adapter gripper mechanism (not shown), thus shifting the adapters 121 on which samples are loaded, from the adapter installation holding turntable mechanism 120 to the adapter bucket mechanism 110 of the centrifuge 100 (adapter shifting step 512). After the shifting operation of the adapters 121 is completed, the centrifuge 100 is controlled to start centrifugal operation (centrifugation operation start step 513).

After centrifuge operation is started, the adapters 121 left on the adapter holding mechanism 120 are shifted to the positions that are emptied by the shifting operation of the adapters 121 by the adapter gripper mechanism (step 514). This is for the purpose of improving the processing speed of the device by reducing the moving operation distance of the sample chuck mechanism when shifting the sample arriving at the centrifuge module, from the carrier 90 to the adapter 121. Similarly, when the centrifuged sample is shifted to the carrier 90 by the sample chuck mechanism after the sample installation adapter 121 on which centrifugal operation is complete is shifted to the adapter holding mechanism 120 by the adapter gripper mechanism, the moving operation distance of the sample shuck mechanism can be reduced and therefore control that contributes to improvement in the processing speed of the device is realized.

After the adapter is shifted in the step 514, the processing shifts to the sample carrier ID acquisition step 502 and a sample forming the next centrifuge set is shifted onto the adapter.

Meanwhile, if it is determined in the post-shifting processing determination step 508 that the sample is not the final sample forming the centrifuge set (in the case of No), it means that there is a remaining sample that forms the centrifuge set but is not yet shifted to the adapter. Therefore, time-out monitoring processing needs to be executed. In this case, the setting of time-out monitoring during centrifugal operation 605 is confirmed in the step 515. If the setting of time-out monitoring during centrifugal operation 605 is set to "valid", time-out monitoring is carried out until the next sample to be processed in the centrifuge module 300 in question arrives, and the time-out time is updated every predetermined period (time-out update step 509). If the absence of arrival of the next sample continues and a time-out occurs (time-out occurrence determination step 510), the centrifuge set is regarded as being finalized even if there is an empty place on the adapter 121 where a sample can be installed, and the adapter shifting step 512 and the centrifugation operation start step 513 are executed.

If the next sample arrives before the occurrence of a time-out (step 511), the accumulated time-out time is cleared, the processing shifts to the sample carrier ID acquisition step 502 and the similar processing is repeated subsequently.

If the setting of time-out monitoring during centrifugal operation 605 is set to "invalid", whether the centrifugal operation of the centrifuge module is in progress or not is determined (step 516). If the centrifugal operation is not in progress, similar processing to the case where the setting of time-out monitoring during centrifugal operation 605 is set to "valid" is carried out. If the centrifugal operation is in progress, arrival of the next sample is waited for, without carrying out the time-out update step 509 and the time-out occurrence monitoring step 510. Also, even in the case where the setting of time-out monitoring during centrifugal operation 605 is set to "invalid" in this manner, as the centrifugal operation by the centrifuge ends, the processing shifts from the step 516 to the time-out update step 509 and the time-out generation monitoring step 510. Therefore, if the next sample does not arrive, the centrifuge set is finalized on the generation of a time-out.

In this example, the adapter holding mechanism can hold eight adapters 121 at maximum. Also, the carrier 90 carrying a sample to the centrifuge module 300 is carried to the empty carrier circulation conveyer line 22 after extraction of the loaded sample, and is used for supply operation of a sample again.

As the processing is carried out according to the flow as described above, if the centrifuge set is finalized even if there is an empty place to install a sample on the adapter 121 after samples are shifted, or if there is no longer any place on the adapter 121 where an arriving sample can be installed, the centrifuge set is finalized without shifting the next sample. Therefore, centrifugal processing can be executed quickly.

At the time point when centrifugal operation is completed, the adapter 121 is taken out from the adapter bucket mechanism 110 held in the centrifuge 100 to the adapter holding mechanism 120 by the adapter gripper mechanism. Since the sample on which centrifugation is complete is loaded on the adapter 121, this sample is taken out and loaded on the carrier 90 by the sample chuck mechanism.

The carrier 90 used to take out the sample on which centrifugal operation is complete from the centrifuge module 300 is supplied from the empty carrier circulation conveyer line 22 to an arriving sample stopper mechanism 43, and the ID information is read by the sample carrier ID reading mechanism 32. After the reading of the ID information of the carrier 90 is completed, the sample of the sample installation adapter 121 is shifted to the carrier 90 by the sample shuck mechanism. Also, while the container in which the sample is housed is rotated by a sample restraining and rotating mechanism 61, the barcode pasted on the sample tube is read by the sample barcode reader 71, thus recognizing the sample ID of the sample that is taken out. The sample ID, the sample attribute, and the carrier ID are reported as one piece of associated information to the operation unit computer 1 and stored in the operation unit computer 1.

Here, the re-recognition of the sample ID of the sample is for the purpose of consistency with the sample information during the carrying control, because there are cases where the sample conveying carrier 90 with the sample loaded thereon may be different from the carrier used at the time point when the sample arrives at the centrifuge module 300, or where samples may be taken out from the centrifuge module 300 in a different order from the arriving order of the samples arriving at the centrifuge module 300. Also, the reason for the difference between the order in which samples arrive at the centrifuge module 300 and the order in which the samples are taken out from the centrifuge module 300 is to perform control to take out a STAT sample preferentially in the case where routine samples and a STAT sample are installed in a mixed manner on the sample installation adapter 121.

Example 2

In this example, a method of finalizing a centrifuge set on the basis of an instruction from the operator will be described.

In the case of this example, the system has an input unit which gives an instruction on finalization of a centrifuge set. As the input unit, a method in which a button displayed on the operation unit computer display 2 is designated via the interface 3 such as a mouse or keyboard may be employed, or a button provided near the input buffer module 200 or the centrifuge module 300 may be pressed to finalize a centrifuge set.

The operator inputs a tray on which only STAT samples are placed, into the input buffer module 200, and makes input via the input unit. As the operation unit computer 1 recognizes the instruction via the input unit, the operation unit computer 1 preferentially starts shifting the samples from the tray in question to a holder, adds the STAT samples placed on the tray in question to the centrifuge set, and then finalizes this centrifuge set. After predetermined processing is carried out, the samples are shifted to the centrifuge module 300. The sample tubes are shifted into the adapter 121, and centrifugal processing is started.

According to this example, a centrifuge set can be finalized at a timing intended by the operator. Therefore, the example is particularly effective in the case where a STAT sample to be processed quickly is carried.

Example 3

In this example, a method of finalizing a centrifuge set on the basis of requested test orders on a sample will be described.

At the time of the sample attribution determination in the step 407 or step 504, requested test orders on the sample in question are recognized, using the sample ID as key information. If a specific test order that is designated in advance is included in the test orders, time-out processing is carried out and the centrifuge set is finalized with this sample.

In the case of this example, an input screen for designating the sample ID to finalize the centrifuge set may be displayed on the operation unit computer 1. Even for routine samples other than STAT samples, this example is particularly effective in the case where there is a test order the result of which needs to be reported urgently.

REFERENCE SIGNS LIST

1: operation unit computer
2: operation unit computer display
3: interface
10: installation tray
20: sample conveyer line
21: overtaking conveyer line
22: empty carrier circulation conveyer line
23: overtaking conveyer merging line
24: empty carrier supply conveyer line
25: routine sample empty carrier supply conveyer line
26: STAT sample empty carrier supply conveyer line
30, 31, 32: sample carrier ID reading mechanism
40, 42, 43, 44, 45: arriving sample stopper mechanism
50, 51, 52, 53: sample carrier conveyer diverging mechanism
60, 61: sample restraining and rotating mechanism
70, 71: sample barcode reader
80: weight measurement mechanism
90: sample conveying carrier
100: centrifuge
110: adapter bucket mechanism
120: adapter installation holding turntable mechanism
121: sample installation adapter
200: input buffer module
210: carrier stocker
300: centrifuge module
401: sample carrier input step
402: sample carrier ID acquisition step
403: sample input position determination step
404: sample input step
405: sample weight measurement step
406: sample ID acquisition step
407: sample attribute determination step
408, 409: time-out setting step
410: centrifuge set information update step
411: centrifuge set information determination step
412: time-out update step
413: time-out occurrence determination step
414: next input sample detection determination step
415: centrifuge set information finalization step
501: sample arrival detection step
502: sample carrier ID acquisition step
503: centrifuge set information acquisition step
504: sample attribute determination step
505, 506: time-out setting step
507: sample shifting step
508: post-shifting processing determination step
509: time-out update step
510: time-out occurrence determination step
511: next arriving sample detection determination step
512: adapter shifting step
513: centrifugation operation start step
514: sample installation adapter shifting step
600: sample input interval time-out setting screen
601: time-out determination position designation
602: routine sample time-out time designation
603: STAT sample time-out time designation

The invention claimed is:

1. A specimen processing system comprising:
an input buffer module which inputs a sample into the system;
a centrifuge module capable of holding plural adapters with samples loaded thereon and performing centrifugal processing simultaneously on the samples held on the adapters;
a sample identification unit which is provided on a sample conveying path and identifies a sample;
a centrifuge set setting unit which sets a group of samples on which centrifugal processing is simultaneously performed by the centrifuge module, as a centrifuge set, on the basis of a time interval at which the sample identification unit identifies samples:
a unit which finalizes the centrifuge set that is set by the centrifugal set setting unit; and
a sample shifting unit which shifts a sample set as the finalized centrifuge set, to the adapters on which centrifugal processing is performed simultaneously by the centrifuge module.

2. The specimen processing system according to claim 1, wherein the sample identification unit is a sample input monitoring unit for monitoring input of a sample into the input buffer module.

3. The specimen processing system according to claim 1, wherein the sample identification unit is, a sample arrival monitoring unit which monitors arrival of a sample at the centrifuge module.

4. The specimen processing system according to claim 1, comprising a weight information acquisition unit which acquires information about weight of individual samples, wherein the centrifuge set setting unit sets the centrifuge set in such a way as to take a balance of weights of the adapters on which centrifugal processing is performed simultaneously.

5. The specimen processing system according to claim 1, comprising:
   an attribute discrimination unit which discriminates an attribute of a sample; and
   a time-out determination unit which sets a time-out time with respect to the centrifuge set setting unit on the basis of the attribute of the sample;
   wherein if a next sample is not identified by the sample identification unit even after the lapse of the time-out time set by the time-out setting unit, the centrifuge set that is set by the centrifuge set setting unit is finalized.

6. The specimen processing system according to claim 5, wherein the attribute discrimination unit discriminates sample attributes including a routine sample and a STAT sample, and
   the time-out determination unit sets a time-out time for the STAT sample to be shorter than for the routine sample.

7. The specimen processing system according to claim 5, comprising a selection unit which selects whether to perform monitoring of the time-out set by the time-out setting unit or not, while the centrifuge module executes centrifugal processing.

8. A processing method for a centrifuge system comprising
   a sample input unit which inputs a sample into the system, and
   a centrifuge unit which performs centrifugal processing on the inputted sample,
   the method comprising:
   a step of identifying a sample;
   a step of measuring weight of the sample;
   a step of setting a group of samples on which centrifugal processing is simultaneously performed, as a centrifuge set, on the basis of information about the weight of the sample;
   a step of determining whether the samples set as the centrifuge set reach a predetermined number or not; and
   a step of finalizing the centrifuge set if the samples set as the centrifuge set in the determination step reach the predetermined number;
   a step of, if the samples set as the centrifuge set do not reach a maximum number in the step, determining whether the centrifuge set can be finalized or not on the basis of an input interval of samples to the sample input unit or an arrival interval of samples to the centrifuge unit.

9. The processing method for the centrifuge system according to claim 8, comprising:
   a step of discriminating an attribute of the inputted sample;
   a step of setting a time-out time to finalize the centrifuge set on the basis of the discriminated attribute; and
   finalizing the centrifuge set on the basis of the time-out time that is set.

10. The processing method for the centrifuge system according to claim 9, wherein the time-out time for a STAT sample is set to be shorter than for a routine sample.

11. The processing method for the centrifuge system according to claim 8, wherein finalization processing of the centrifuge set based on the time-out time is not executed on a next centrifuge set while the centrifuge unit executes centrifugal processing on the finalized centrifuge set.

* * * * *